(12) United States Patent
Adams et al.

(10) Patent No.: US 7,141,421 B2
(45) Date of Patent: Nov. 28, 2006

(54) CONTROL OF METABOLISM WITH HUMAN 2-OXOGLUTARATE CARRIER

(75) Inventors: Sean H. Adams, Randolph Township, NJ (US); Xing Xian Yu, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/888,264

(22) Filed: Jun. 22, 2001

(65) Prior Publication Data

US 2002/0103150 A1    Aug. 1, 2002

Related U.S. Application Data

(60) Provisional application No. 60/213,307, filed on Jun. 22, 2000.

(51) Int. Cl.
*C12N 5/00*    (2006.01)

(52) U.S. Cl. ............................. 435/375; 435/3; 435/4; 435/6; 435/7.1

(58) Field of Classification Search ................ 435/7.1, 435/4, 6, 3, 375
See application file for complete search history.

(56) References Cited

U.S. PATENT DOCUMENTS

| 5,364,934 A | 11/1994 | Drayna et al. |
| 6,132,973 A | 10/2000 | Lal et al. |

FOREIGN PATENT DOCUMENTS

| WO | WO 99/00123 | 1/1999 |
| WO | WO 99/00123 A1 | 1/1999 |
| WO | WO 99/64458 | 12/1999 |
| WO | WO 99/64458 A1 | 12/1999 |
| WO | WO 00/04037 A1 | 1/2000 |
| WO | WO 00/61614 A2 | 10/2000 |
| WO | WO 01/98355 A2 | 12/2001 |
| WO | WO 01/98512 A2 | 12/2001 |

OTHER PUBLICATIONS

Appleby, R.D. et al. Quantitation and origin of the mitochondrial membrane potential in human cells lacking mitochondrial DNA (Eur. J. Biochem. vol. 262, p. 108-116; May 1999).*
Guo et al. American Journal of Physiology, 1999, pp. L1018-L1026.*
Daniel et al. Neurogastroenterol. Mot., 2001, pp. 297-307.*
A Palmisano et al., J. Biochem.,"Targeting and assembly of the oxoglutarate carrier: general principles for biogenesis of carrier proteins of the mitochondrial inner membrane," 1998, 333, pp. 151-158.*
Xing Xian Yu, et al., 2001. Overexpression of the human 2-oxoglutarate carrier lowers mitochondrial membrane potential in HEK-293 cells: contrast with the unique cold-induced mitochondrial carrier CGI-69, *Biochem. J.*, 353:369-375.

Zhang, Chen-Yu, et al., 1999. Assessment of uncoupling activity of uncoupling protein 3 using a yeast heterologous expression system, *Fed. Of Euro. Biochem. Soc.*, 449:129-134.
DAS, Kallol, et al., 1999. Predominant expression of the mitochondrial dicarboxylate carrier in white adipose tissue, *Biochem J.*, 344:313-320.
Walker, John E. and M.J. Runswick, 1993. The Mitochondrial Transport Protein Superfamily, *J. of Bioenergetics and Biomembranes*, 25:435-446.
Jezek, Petr, et al., 1998. Fatty acid cycling mechanism and mitochondrial uncoupling proteins, *Biochimica et Biophysica Acta.*, 1365:319-327.
Anderson, B., et al., Genbank Accession AF070548. Aug. 1998.
Tisdale, M., "Cancer Cachexia: Metabolic Alterations and Clinical Manifestations," *Nutrition*, 13:1-7 (1997) (complete reference herewith submitted).
Adams, S., "Uncoupling Protein Homologs: Emerging Views of Physiological Function," *J. Nutr.* 130:711-714 (2000).
Boss, O., S. Samec, A. Paoloni-Giacobino, C. Rossier, et al., "Uncoupling protein-3: a new member of the mitochondrial carrier family with tissue-specific expression," *FEBS Letters*, 408:39-42 (1997).
Bouillaud, F., D. Ricquier, J. Thibault, and J. Weissenbach, "Molecular Approach to Thermogenesis in Brown Adipose Tissue: cDNA Cloning of the Mitochondrial Uncoupling Protein," *Proc. Natl. Acad. Sci.*, 82(2):445-448 (1985).
Brand, M., L. Chien, E. Ainscow, D. Rolfe, et al., "The causes and functions of mitochondrial proton leak," *Biochim. Biophys. Acta.*, 1187:132-139 (1994).
Bray, G., "Progress in Understanding the Genetics of Obesity." *J Nutr.*, 127:940S-942S (1997).
Carter, P., H. Bedouelle, and G. Winter, "Improved oligonucleotide site-directed mutagenesis using M13 vectors," *Nucl. Acids Res.*, 13:4431-4443 (1985).
Cassard, A., F. Bouillaud, M. Mattei, E. Hentz, et al., "Human Uncoupling Protein Gene: Structure, Comparison With Rat Gene, and Assignment to the Long Arm of Chromosome 4," *J. Cell Biochem.*, 43:255-264 (1990).
Chothia, C., "The Nature of the Accessible and Buried Surfaces in Proteins," *J. Mol. Biol.*, 105:1-14 (1976).
Creighton, "Posttranslational Covalent Modifications of Polypeptide Chains," in "Proteins: Structure and Molecular Properties," (W.H., Freeman & Co.) (San Fran., CA), pp. 78-86 (1983).
Cunningham, B. and J. Wells, "High-Resolution Epitope Mapping of hGH-Receptor Interactions by Alanine-Scanning Mutagenesis," *Science*, 244:1081-1085 (1989).
Fleury, C., M. Neverova, S. Collins, S. Raimbault, et al., "Uncoupling protein-2: a novel gene linked to obesity and hyperinsulinemia," *Nat. Genet.*, 15:269-272 (1997).

(Continued)

*Primary Examiner*—Anne-Marie Falk
*Assistant Examiner*—Jon Eric Angell
(74) *Attorney, Agent, or Firm*—Merchant & Gould P.C.

(57) ABSTRACT

The present invention is directed to compositions and methods related to the use of human OGC as an uncoupling protein.

10 Claims, No Drawings

OTHER PUBLICATIONS

Gimeno, R., M. Dembski, X. Weng, N. Deng, et al., "Cloning and Characterization of an Uncoupling Protein Homolog. A Potential Molecular Mediator of Human Thermogenesis," *Diabetes*, 46:900-906 (1997).

Goldstein, S. and D. Elwyn, "The effects of injury and sepsis on fuel utilization," *Annu. Rev. Nutr.*, 9:445-473 (1989).

Gong, D., Y. He, M. Karas, and M. Reitman, "Uncoupling Protein-3 Is a Mediator of Thermogenesis Regulated by Thyroid Hormone, β3-Adrenergic Agonists, and Leptin," *J. Biol. Chem.*, 272(39):24129-24132 (1997).

Gura, T., "Uncoupling Proteins Provide New Clue to Obesity's Causes," *Science*, 280:1369-1370 (1998).

Hill, J. and J. Peters, "Environmental Contributions to the Obesity Epidemic," *Science*, 280:1371-1374 (1998).

Iacobazzi, V., et al. GenBank Accession No. NM_003562 (1992).

Iacodazzi, V., F. Palmieri, M. Runswick, and J. Walker, "Sequences of the human and bovine genes for the mitochondrial 2-oxoglutarate carrier," *DNA Seq.*, 3(2):79-88 (1992).

Jacobsson, A., U. Stadler, M. Glotzer, and L. Kozak, "Mitochondrial Uncoupling Protein from Mouse Brown Fat," *J. Biol. Chem.*, 260(30):16250-16254 (1985).

Ježek, P., H. Engstova, M. Zackova, A. Vercesi, et al., "Fatty acid cycling mechanism and mitochondrial uncoupling proteins," *Biochim. Biophys. Acta.*, 1365:319-327 (1998).

Kallol, D., R. Lewis, T. Combatsiaris, Y. Lin, et al., "Predominant expression of the mitochondrial dicarboxylate carrier in white adipose tissue," *Biochem. J.*, 344:313-320 (1999).

Kinney, J., J. Duke, Jr., C. Long, and F. Gump, "Tissue fuel and weight loss after injury." *J. Clin. Path.*, 23(4):65-72 (1970).

Lai, C., C. Chou, L. Ch'ang, C. Liu, and C. Liu, et al., GenBank Accession No. AF151827 (2000).

Lai, C., C. Chou, L. Ch'ang, C. Liu, and W. Lin, "Identification of Novel Human Genes Evolutionarily Conserved in *Caenorhabditis elegans* by Comparative Proteomics," *Genome Res.*, 10:703-713 (2000).

Mao, W., X. Yu, A. Zhong, W. Li, et al. "UCP4, a novel brain-specific mitochondrial protein that reduces membrane potential in mammalian cells," *FEBS Lett.* 443:326-330 (1999).

Must, A., J. Spadano, E. Coakley, A.E. Field, et al. "The Disease Burden Associated With Overweight And Obesity." *JAMA.*, 282:1523-1529 (1999).

Nicholls, D. and R. Locke, "Thermogenic Mechanisms in Brown Fat," *Physiol. Rev.*, 64:1-64 (1984).

Palmieri, F., F. Bisaccia, L. Capobianco, V. Dolce, et al., "Transmembrane Topology, Genes, and Biogenesis of the Mitochondrial Phosphate and Oxoglutarate Carriers," *J. Bioenerg. Biomemb.*, 25(5)493-501 (1993).

Palmisano, A., V. Zara, A. Hönlinger, A. Vozza, et al., "Targeting and assembly of the oxoglutarate carrier: general principles for biogenesis of carrier proteins of the mitochondrial inner membrane," *Biochem J.* 333:151-158 (1998).

Piccininni, S., V. Iacobazzi, G. Lauria, M. Rocchi, and F. Palmieri, "Assignment of the oxoglutarate carrier gene (SLC20A4) to human chromosome 17p13.3," *Cytogenet. Cell Genet.*, 83:256-257 (1998).

Poutska, A., M. Klein, H. Mewes, J. Gassenhuber, and S. Wiemann, GenBank Accession No. AL133584 (1999).

Ricquier, D., L. Casteilla, and F. Bouillaud, "Molecular studies of the uncoupling protein," *FASEB J,.* 5:2237-2242 (1991).

Rolfe, D., A. Hulbert, and M. Brand, "Characteristics of mitochondrial proton leak and control of oxidative phosphorylation in the major oxygen-consuming tissues of the rat," *Bicohim. Biophys. Acta.*, 1118:405-416 (1994).

Rolfe, D., J. Newman, J. Buckingham, M. Clark, et al. "Contribution of mitochondrial proton leak to respiration rate in working skeletal muscle and liver and to SMR," *Am. J. Physiol.*, 276:C692-C699 (1999).

Runswick, M., J. Walker, F. Bisaccia, V. Iacobazzi, and F. Palmieri, GenBank Accession No. AAA30672 (1990).

Sanchis, D., C. Fleury, N. Chomiki, M. Goubern, et al., "BMCP1, a Novel Mitochondrial Carrier with High Expression in the Central Nervous System of Humans and Rodents, and Respiration Uncoupling Activity in Recombinant Yeast," *J. Biol. Chem.*, 273(51):34611-34615 (1998).

Shimkets, R., D. Lowe, J. Tai, P. Sehl, et al., "Gene expression analysis by transcript profiling coupled to a gene database query," *Nat. Biotechnol.*, 17:798-803.

Solanes, G., A. Vidal-Puig, D. Grujic, J. Flier, and B. Lowell, "The Human Uncoupling Protein-3 Gene," *J. Biol. Chem.*, 272(41):25433-25436 (1997).

Vidal-Puig, A., G. Solanes, D. Grujic, J. Flier, et al., "UCP3: An Uncoupling Protein Homologue Expressed Preferentially and Abundantly in Skeletal Muscle and Brown Adipose Tissue," *Biochem. Biophys. Res. Comm.*, 235:79-82 (1997).

Walker, J. and M. Runswick, "The Mitochondrial Transport Protein Superfamily," *J. Bioenerg. Biomemb.*, 25(5):435-446 (1993).

Wells, J., M. Vasser, and D. Powers, "Cassette mutagenesis: an efficient method for generation of multiple mutations at defined sites," *Gene*, 34:315-323 (1985).

Wells, J., B. Cunningham, T. Graycar, and D. Estell, "Importance of Hydrogen-Bond Formation in Stabilizing the Transition State of Subtilisin," *Philos. Trans. R. Soc. London Ser. A,*, 317:415-423 (1986).

Wolf, G., "A New Uncoupling Protein: A Potential Component of the Human Body Weight Regulation System," *Nutr. Rev.*, 55:178-179 (1997).

Yu, X., J. Barger, B. Boyer, M. Brand, et al., "Impact of endotoxin on UCP homolog mRNA abundance, thermoregulation, and mitochondrial proton leak kinetics," *Am. J. Physiol. Endocrinol. Metab.* 279:E433-E446 (2000).

Yu, X., W. Mao, A. Zhong, P. Schow, et al., "Characterization of novel UCP5/BMCP1 isoforms and differential regulation of UCP4 and UCP5 expression through dietary or temperature manipulation." *FASEB J.*, 14:1611-1618 (2000).

Zhang, C., T. Hagen, V. Mootha, L. Slieker, and B. Lowell, "Assessment of uncoupling activity of uncoupling protein 3 using a yeast heterologous expression system," *FEBS Lett.*, 449:129-134 (1999).

Zoller, M. and M. Smith, "Oligonucleotide-directed mutagenesis using M13-derived vectors: an efficient and general procedure for the production of point mutations in any fragment of DNA," *Nucl. Acids Res.*, 10:6487-6501 (1982).

Bing et al., "Increased Gene Expression of Brown Fat Uncoupling Protein (UCP)1 and Skeletal Muscle UCP2 and UCP3 in MAC16-induced Cancer Cachexia", *Cancer Research*, 60:2405-2410 (2000).

GenBank Accession NM_016016 (2000).

Huizing et al., "Human Mitochondrial Transmembrane Metabolite Carriers: Tissue Distribution and Its Implication for Mitochondrial Disorders", *Journal of Bioenergetics and Biomembranes*, 30(3):277-184.

Ledesma et al., "The mitochondrial uncoupling proteins", *Geneome Biology*, 3(12):3015.1-3015.9 (2002).

Vidal-Puig et al., "Energy Metbolism in Uncoupling Protein 3 Gene Knockout Mice", *The Journal of Biological Chemistry*, 275(21):16258-16266 (2000).

NCBI Blast Search of AAC28637 dated Jul. 30, 2004 (Exhibit A).

NCBI Conserved Domain Search AAC28637 dated Jul. 29, 2004 (Exhibit B).

GenBank Accession No. AAC28637 dated Aug. 5, 1998.

Scholz et al., "Ontogeny of malate-aspartate shuttle capacity and gene expression in cardiac mitochondira", *Am. J. Physiol.*, 274 (Cell Physiol. 43): C780-C788 (1998).

European Search Report, dated Nov. 23, 2004.

* cited by examiner

SEQUENCE LISTING

<160> NUMBER OF SEQ ID NOS: 2

<210> SEQ ID NO 1
<211> LENGTH: 1123
<212> TYPE: DNA
<213> ORGANISM: Homo sapiens; GenBank NM_003562

<400> SEQUENCE: 1
ccgagggcca ttgagtggcg atggcggcga cggcgagtgc cggggccggc gggatggacg    60

-continued

```
ggaagcccccg tacctccccct aagtccgtca agttcctgtt tgggggcctg gccgggatgg      120
gagctacagt ttttgtccag cccctggacc tggtgaagaa ccggatgcag ttgagcgggg      180
aaggggccaa gactcgagag tacaaaacca gcttccatgc cctcaccagt atcctgaagg      240
cagaaggcct gagggggcatt tacactgggc tgtcggctgg cctgctgcgt caggccacct      300
acaccactac ccgccttggc atctataccg tgctgtttga gcgcctgact ggggctgatg      360
gtactccccc tggctttctg ctgaaggctg tgattggcat gaccgcaggt gccactggtg      420
cctttgtggg aacaccagcc gaagtggctc ttatccgcat gactgccgat ggccggcttc      480
cagctgacca gcgccgtggc tacaaaaatg tgtttaacgc cctgattcga atcacccggg      540
aagagggtgt cctcacactg tggcggggct gcatccctac catggctcgg gccgtcgtcg      600
tcaatgctgc ccagctcgcc tcctactccc aatccaagca gttcttactg gactcaggct      660
acttctctga acatatcctg tgccacttct gtgccagcat gatcagcggt cttgtcacca      720
ctgctgcctc catgcctgtg gacattgcca agacccgaat ccagaacatg cggatgattg      780
atgggaagcc ggaatacaag aacgggctgg acgtgctgtt caaagttgtc cgctacgagg      840
gcttcttcag cctgtggaag gcttcacgc cgtactatgc ccgcctgggc ccccacaccg      900
tcctcacctt catcttcttg gagcagatga acaaggccta caagcgtctc ttcctcagtg      960
gctgaagcgt tcagggcac acaggacagc agaagatccc ctttgtcagt ggggaaacca     1020
aggcagagct gaggggacag ggaggagcag aagccatcaa gatggtcaaa gggcctgcag     1080
agggagatgt ggccttcctc ccccctcattg aggactcaat aaa                       1123
```

<210> SEQ ID NO 2
<211> LENGTH: 1503
<212> TYPE: DNA
<213> ORGANISM: Homo sapiens; GenBank AF070548

<400> SEQUENCE: 2

```
cctcgtgcca ggcgtgcgcg cgccctcgct ctgttgcgcg cgcggtgtca ccttgggcgc        60
gagcggggcc gtgcgcgcac gggacccgga gccgagggcc attgagtggc gatggcggcg      120
acggcgagtg ccggggccgg cgggatagac gggaagcccc gtacctcccc taagtccgtc      180
aagttcctgt ttgggggcct ggccgggatg ggagctacag ttttgtccag cccctggac      240
ctggtgaaga accggatgca gttgagcggg gaaggggcca agactcgaga gtacaaaacc      300
agcttccatg ccctcaccag tatcctgaag gcagaaggcc tgagggggcat ttacactggg      360
ctgtcggctg gcctgctgcg tcaggccacc tacaccacta cccgccttgg catctatacc      420
gtgctgtttg agcgcctgac tggggctgat ggtactcccc ctggctttct gctgaaggct      480
gtgattggca tgaccgcagg tgccactggt gcctttgtgg gaacaccagc cgaagtggct      540
cttatccgca tgactgccga tggccggctt ccagctgacc agcgccgtgg ctacaaaaat      600
gtgtttaacg ccctgattcg aatcacccgg gaagagggtgt cctcacactg tggcggggc      660
tgcatcccta ccatggctcg ggccgtcgtc gtcaatgctg cccagctcgc ctcctactcc      720
caatccaagc agttcttact ggactcaggc tacttctctg acaacatctt gtgccacttc      780
tgtgccagca tgatcagcgg tcttgtcacc actgctgcct ccatgcctgt ggacattgcc      840
aagacccgaa tccagaacat gcggatgatt gatgggaagc cggaatacaa gaacgggctg      900
gacgtgctgt tcaaagttgt ccgctacgag ggcttcttca gcctgtggaa ggcttcacg      960
ccgtactatg cccgcctggg ccccacaccc gtcctcacct tcatcttctt ggagcagatg     1020
aacaaggcct acaagcgtct cttcctcagt ggctgaagcg gccgggggct cccactcgcc     1080
```

```
tgctgcgcct atagccactg cgccctgggg gcctgggctc tgctgccctg gaccoctcta    1140 tttatttccc ttccacagtg tggtttcttc ctctgcggta aaggacttgg tctgttctac    1200
cccctgctcc agcttgccct gctcgtcctg atcctgtgat ttctctgtcc ttggctattc    1260
ttgcagggag ctggaaaact tcctgaggat ttctggcctc cccctgggtt ttagtttcag    1320
ggcacacagg acagcagaag atccoctttg tcagtgggga aaccaaggca gagctgaggg    1380
gacagggagg agcagaagcc atcaagatgg tcaaagggcc tgcagaggga gatgtggccc    1440
ttcctccccc tcattgagga cttaataaat tggattgatg acaccaaaaa aaaaaaaaaa    1500
aaa                                                                  1503
```

CONTROL OF METABOLISM WITH HUMAN 2-OXOGLUTARATE CARRIER

RELATED APPLICATIONS

This application claims priority to U.S. Provisional Application Ser. No. 60/213,307, filed Jun. 22, 2000, which is incorporated herein by reference in its entirety.

BACKGROUND OF THE INVENTION

The bulk of animal tissue oxygen consumption is driven by a finely-balanced system in which the rate of mitochondrial catabolism of fuels is regulated largely by the flow of electrons along the electron-transport chain. Concomitant pumping of protons outward across the mitochondrial inner membrane establishes a proton electrochemical gradient or proton motive force ($\Delta p$) which drives ATP synthesis via inward flow of protons through $F_1F_0$ ATP synthase. Thus, fuel combustion, electron transport, proton flux, and ATP turnover are intimately coupled. However, a portion of the $\Delta p$ is dissipated as protons flow inward independent of ATP synthase, a phenomenon termed "proton leak" or "uncoupling." Fuel combustion and electron transport/outward proton pumping increase in response to dissipation of $\Delta p$; thus, innate mitochondrial proton leak may account for a significant amount of daily energy expenditure (estimated at between 20–40% of tissue metabolic rate)[Brand et al, Biochim. Biophys. Acta, 1187:132–139 (1994); Rolfe et al., Am. J. Physiol., 276:C692–C699 (1999)].

The first indication that specific proteins may underlie mammalian mitochondrial proton leak emerged from studies of brown adipose tissue (BAT), a specialized tissue in which a large proportion of mitochondrial oxygen consumption is uncoupled from ATP synthesis under conditions in which adaptational thermogenesis is triggered (i.e. cold-exposure in rodents)[Nicholls and Locke, Physiol. Rev., 64:1–64 (1984)]. The heat-generating futile cycling of the BAT mitochondrial proton circuit was found to be associated with a specific protein termed uncoupling protein (UCP, subsequently named UCP1)[Nicholls and Locke, supra; Ricquier et al., FASEB J., 5:2237–2242 (1991)].

UCPs were first found and described in the brown fat cells of hibernating animals, such as bears. UCPs were believed to help such hibernators and other cold-weather adapted animals maintain core body temperatures in cold weather by raising their body's resting metabolic rate. Because humans possess relatively small quantities of brown adipose tissue, UCPs were originally thought to play a minor role in human metabolism.

Several different human uncoupling proteins have now been described. [See, generally, Gura, Science, 280:1369–1370 (1998)]. The human uncoupling protein referred to as UCP1 was identified by Nicholls et al. Nicholls et al. showed that the inner membrane of brown fat cell mitochondria was very permeable to proteins, and the investigators traced the observed permeability to a protein, called UCP1, in the mitochondrial membrane. Nicholls et al. reported that the UCP1, by creating such permeability, reduced the number of ATPs that can be made from a food source, thus raising body metabolic rate and generating heat. [Nicholls et al., Physiol. Rev., 64, 1–64 (1984)].

It was later found that UCP1 is indeed expressed only in brown adipose tissue [Bouillaud et al., Proc. Natl. Acad. Sci. 82:445–448 (1985); Jacobsson et al., J. Biol. Chem., 260: 16250–16254 (1985)]. Genetic mapping studies have shown that the human UCP1 gene is located on chromosome 4. [Cassard et al., J. Cell. Biochem., 43:255–264 (1990)].

Despite confinement of UCP1 to BAT under most conditions, significant proton leak occurs in all tissues in which it has been measured, leading to the possibility that UCPs are present body-wide and impact whole-animal metabolic rate. To date, four putative UCP homologs have been identified, with homolog-specific tissue expression patterns [see Adams, J. Nutr., 130:711–714 (2000)].

Another human UCP, referred to as UCPH or UCP2, has also been described. [Gimeno et al., Diabetes, 46:900–906 (1997); Fleury et al., Nat. Genet., 15:269–272 (1997); Boss et al., FEBS Letters, 408:39–42 (1997); see also, Wolf, Nutr. Rev., 55:178–179 (1997)]. Fleury et al. teach that the UCP2 protein has 59% amino acid identity to UCP1, and that UCP2 maps to regions of human chromosome 11 which have been linked to hyperinsulinaemia and obesity. [Fleury et al., supra]. It has also been reported that UCP2 is expressed in a variety of adult tissues, such as brain and muscle and fat cells. [Gimeno et al., supra, and Fleury et al., supra].

A third human UCP, UCP3, was recently described in Boss et al., supra; Vidal-Puig et al., Biochem. Biophys. Res. Comm., 235:79–82 (1997); Solanes et al., J. Biol. Chem., 272:25433–25436 (1997); and Gong et al., J. Biol. Chem., 272:24129–24132 (1997). [See also Great Britain Patent No. 9716886]. Solanes et al. report that unlike UCP1 and UCP2, UCP3 is expressed preferentially in human skeletal muscle, and that the UCP3 gene maps to human chromosome 11, adjacent to the UCP2 gene. [Solanes et al., supra]. Gong et al. describe that the UCP3 expression can be regulated by known thermogenic stimuli, such as thyroid hormone, beta3-andrenergic agonists and leptin. [Gong et al., supra].

To characterize a putative UCP, an in vitro assay measuring mitochondrial membrane potential ($\Delta_{\psi_m}$) may be used. Ectopic expression of UCP homologs in mammalian cell lines and yeast leads to a drop in $\Delta_{\psi_m}$, consistent with uncoupling under these conditions. As a negative control in such experiments, it is preferable to use a molecule that is a mitochondria-localized carrier that exchanges compounds in an electroneutral manner. Human 2-oxoglutarate (human OGC) exhibits these characteristics. Furthermore, it was reported that expression of human OGC in transformed yeast did not affect mitochondrial function [Sanchis et al., J. Biol. Chem. 273(51):34611–34615 (1998)].

BRIEF SUMMARY OF THE INVENTION

It has now been discovered that OGC exhibits the characteristics of a UCP, i.e., changes mitochondrial membrane potential. Based on the published reports of the characteristics of human OGC noted above, it would not have been predicted that over-expression of the molecule in mammalian cells would have an effect on the mitochondrial membrane potential within the cells. However, over-expression of human OGC affects mitochondrial membrane potential at a similar level as known UCPs. Thus, human OGC surprisingly has the characteristics of a UCP.

DETAILED DESCRIPTION OF THE INVENTION

The invention relates to the discovery that human OGC is an uncoupling protein. In certain embodiments, a mammalian cell is contacted with a composition that increases expression or activity of human OGC, wherein the increased expression of human OGC thereby decreases the mitochondrial membrane potential in the cell. When the mammalian cell is contacted in vivo, such compositions and methods are useful for treating a metabolic conditions, such as obesity.

In other embodiments, a mammalian cell is contacted with a composition that decreases expression or activity of human OGC, wherein the decreased expression of human OGC thereby increases the mitochondrial membrane potential in the cell. When the mammalian cell is contacted in vivo, such compositions and methods are useful for treating a metabolic disorder, such as cachexia.

The present invention includes assays for screening compounds or compositions for the ability to alter mitochondrial membrane potential. Such compounds or compositions are excellent candidates as therapeutics for metabolic conditions. Such compositions may include small molecules. When the composition encodes a variant of human OGC, the assay may be used to determine whether the variant maintains, has an increase in, or has a decrease in the ability to alter mitochondrial membrane potential as compared to a native human OGC. Furthermore, alternative native forms may be compared to each other.

Also described herein are diagnostic methods and kits for detecting a metabolic disorder. In certain embodiments, the method comprises detecting human OGC expression, or lack thereof, in a cell or tissue sample. In other embodiments, the method detects an alteration in the sequence of human OGC causing an alteration in human OGC activity or an alteration in the genome affecting the expression of human OGC.

Greater description of these embodiments and others are described below. Furthermore, in light of the present disclosure, additional embodiments will be apparent to those of skill in the art.

I. Definitions

The terms "human OGC polypeptide", "human OGC protein" and "human OGC" when used herein encompass native sequence human OGC and human OGC variants (which are further defined herein). The human OGC may be isolated from a variety of sources, such as from human tissue types or from another source, or prepared by recombinant and/or synthetic methods.

A "native sequence human OGC" comprises a polypeptide having the same amino acid sequence as a human OGC derived from nature. Such native sequence human OGC can be isolated from nature or can be produced by recombinant and/or synthetic means. The term "native sequence human OGC" specifically encompasses naturally-occurring truncated forms or isoforms, naturally-occurring variant forms (e.g., alternatively spliced forms) and naturally-occurring allelic variants of the human OGC. In one embodiment of the invention, the native sequence human OGC is a mature or full-length human native sequence. Several such sequences are known in the art and include those encoded by the nucleic acids of GenBank accession numbers NM_003562 and AF070548. There is a single nucleotide difference between NM_003562 and AF070548 (G to A) at position 36 (relative to the start ATG) resulting in a change in the respective proteins at position 12 (M to I).

"Human OGC variant" means anything other than a native sequence human OGC, and includes human OGC having at least about 80% amino acid sequence identity with the amino acid sequence of a native human OGC. Such human OGC variants include, for instance, human OGC polypeptides wherein one or more amino acid residues are added, or deleted, at the N- or C-terminus, as well as within one or more internal domains. Ordinarily, a human OGC variant will have at least about 80% amino acid sequence identity, more preferably at least about 85% amino acid sequence identity, even more preferably at least about 90% amino acid sequence identity, and most preferably at least about 95% sequence identity with the amino acid sequence of a native human OGC.

"Percent (%) amino acid sequence identity" with respect to the human OGC sequences identified herein is defined as the percentage of amino acid residues in human OGC sequence that are identical with the amino acid residues in the candidate sequence, after aligning the sequences and introducing gaps, if necessary, to achieve the maximum percent sequence identity, and not considering any conservative substitutions as part of the sequence identity. % identity can be determined by WU-BLAST-2 (Altschul et. al., 1996, *Methods in Enzymology*, 266: 460–480). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored.

The term "positives", in the context of sequence comparison performed as described above, includes residues in the sequences compared that are not identical but have similar properties (e.g. as a result of conservative substitutions). The % value of positives is determined by the fraction of residues scoring a positive value in the BLOSUM 62 matrix divided by the total number of residues in the longer sequence, as defined above.

In a similar manner, "percent (%) nucleic acid sequence identity" is defined as the percentage of nucleotides in human OGC sequence that are identical with the nucleotides in the candidate sequence. The identity values can be generated by the BLASTN module of WU-BLAST-2 set to the default parameters, with overlap span and overlap fraction set to 1 and 0.125, respectively.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the human OGC natural environment will not be present. Ordinarily, however, isolated polypeptide will be prepared by at least one purification step.

An "isolated" nucleic acid molecule encoding a human OGC polypeptide is a nucleic acid molecule that is identified and separated from at least one contaminant nucleic acid molecule with which it is ordinarily associated in the natural source of the human OGC-encoding nucleic acid. An isolated human OGC-encoding nucleic acid molecule is other than in the form or setting in which it is found in nature. Isolated nucleic acid molecules therefore are distinguished from the human OGC-encoding nucleic acid molecule as it exists in natural cells. However, an isolated nucleic acid molecule encoding a human OGC polypeptide includes human OGC-encoding nucleic acid molecules contained in cells that ordinarily express human OGC where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-human OGC monoclonal antibodies (including agonist, antagonist, and neutralizing antibodies) and anti-human OGC antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C. followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 MM sodium phosphate (pH 7.6), 5× Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising a human OGC polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of human OGC which retain the biologic and/or immunologic activities of native or naturally-occurring human OGC. A preferred activity is the ability to affect mitochondrial membrane potential in a way that results in an up- or down-regulation of metabolic rate and/or heat production. One such activity includes the generation of proton leakage in mitochondrial membrane that results in an increase in metabolic rate.

The term "antagonist" is used in the broadest sense, and includes any molecule that partially or fully blocks, inhibits, or neutralizes a biological activity of a native human OGC polypeptide disclosed herein. In a similar manner, the term "agonist" is used in the broadest sense and includes any molecule that mimics a biological activity of a native human OGC polypeptide disclosed herein. Suitable agonist or antagonist molecules specifically include agonist or antagonist antibodies or antibody fragments, or fragments or amino acid sequence variants of native human OGC polypeptides.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cows, horses, sheep, pigs, etc. Preferably, the mammal is human.

Administration "in combination with" one or more further therapeutic agents includes simultaneous (concurrent) and consecutive administration in any order.

"Metabolic disorders" are diseases, disorders, or symptoms that are associated with metabolic rate and/or heat production. Examples of such disorders include obesity, cachexia, viral infections, cancers, and bacterial infections.

II. Compositions and Methods of the Invention

A. Uses for Human OGC

As disclosed herein, surprisingly, human OGC has uncoupling activity. UCPs are useful in methods of detecting and treating metabolic disorders. Such methods, and others, using UCP compositions are known in the art, e.g. See WO 00/04037.

Nucleotide sequences (or their complement) encoding human OGC have various applications in the art of molecular biology, including uses as hybridization probes, in chromosome and gene mapping and in the generation of antisense RNA and DNA. Human OGC nucleic acid will also be useful for the preparation of human OGC polypeptides by the recombinant techniques described herein.

The full-length native sequence human OGC gene, or fragments thereof, may be used as, among other things, hybridization probes for a cDNA library to isolate the full-length human OGC gene or to isolate still other genes (for instance, those encoding naturally-occurring variants of human OGC or OGC from other species) which have a desired sequence identity to the native human OGC sequence. Optionally, the length of the probes will be about 20 to about 80 bases. The hybridization probes may be derived from the nucleotide sequence of the human OGC coding region or from genomic sequences including promoters, enhancer elements and introns of native sequence human OGC. By way of example, a screening method will comprise isolating the coding region of the human OGC gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the human OGC gene of the present invention can be used to screen libraries of human cDNA, genomic DNA or mRNA to determine which members of such libraries the probe hybridizes to. Hybridization techniques are well known in the art.

The probes may also be employed in PCR techniques to generate a pool of sequences for identification of closely related human OGC coding sequences.

Nucleotide sequences encoding a human OGC can also be used to construct hybridization probes for mapping the gene which encodes that human OGC and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for human OGC encode a protein which binds to another protein, the human OGC can be used in assays to identify the other proteins or molecules involved in the binding interaction. By such methods, inhibitors of the binding interaction can be identified. Proteins involved in such binding interactions can also be used to screen for peptide or small molecule inhibitors or agonists of the binding interaction. Screening assays can be designed to find lead compounds that mimic the biological activity of a native human OGC or a protein that interacts with for human OGC. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode human OGC or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding human OGC can be used to clone genomic DNA encoding human OGC in accordance with established techniques and the genomic sequences used to generate transgenic animals that contain cells which express DNA encoding human OGC. Methods for generating transgenic animals, particularly animals such as mice or rats, have become conventional in the art and are described, for example, in U.S. Pat. Nos. 4,736,866 and 4,870,009. Typically, particular cells would be targeted for human OGC transgene incorporation with tissue-specific enhancers. Transgenic animals that include a copy of a transgene encoding human OGC introduced into the germ line of the animal at an embryonic stage can be used to examine the effect of increased expression of DNA encoding human OGC. Such animals can be used as tester animals for reagents thought to confer protection from, for example, pathological conditions associated with its overexpression or underexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of OGC can be used to construct a OGC "knock out" animal which has a defective or altered gene encoding OGC as a result of homologous recombination between the endogenous gene encoding OGC and altered genomic DNA encoding OGC introduced into an embryonic cell of the animal. For example, cDNA encoding OGC can be used to clone genomic DNA encoding OGC in accordance with established techniques. A portion of the genomic DNA encoding OGC can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the OGC polypeptide.

Nucleic acid encoding the OGC polypeptides, preferably human OGC polypeptides, may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA 83, 4143–4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., Trends in Biotechnology 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429–4432 (1987); and Wagner et al., Proc. Natl. Acad. Sci. USA 87, 3410–3414 (1990). For review of gene marking and gene therapy protocols see Anderson et al., Science 256, 808–813 (1992).

It is believed that the human OGC gene therapy has applications in, for instance, treating metabolic conditions. This can be accomplished, for example, using the techniques described above and by introducing a viral vector containing a human OGC gene into certain tissues (like muscle or fat) to increase metabolic rate in these targeted tissues and thereby elevate energy expenditure.

Generally, methods of treatment employing human OGC are contemplated by the invention. Fuel combustion, electron transport, proton pumping and $O_2$ consumption (which may be referred to collectively as metabolic rate) are coupled to ATP synthesis. There can be an "inefficiency" in mammals, such that a portion of metabolic rate (in some cases which may be greater than 20%) may be ascribed to $H^+$ "leak" back into the matrix space with no ATP synthesis.

As shown in the Examples herein, human OGC is involved in catalyzing $H^+$ leak, thereby playing a role in energetic inefficiency in vivo. Accordingly, modulating human OGC activity or quantities (presence or expression) of human OGC in mammalian tissues (particularly, metabolically important tissues), may concomitantly modulate $H^+$ leak, metabolic rate and heat production. The methods of modulating (either in an up-regulation or down-regulation mode) metabolic rate in a mammal has a variety of therapeutic applications, including treatment of obesity and the symptoms associated with stroke, trauma (such as burn trauma), sepsis and infection.

In the treatment of obesity, those skilled in the art will appreciate that the modulation of mitochonrial membrane potential may be used to increase body metabolic rate, thereby enhancing an individual's ability for weight loss. Screening assays may be conducted to identify molecules which can up-regulate expression or activity (such as the uncoupling) of human OGC. Molecules that up-regulate human OGC activity thereby decrease mitochondrial membrane potential. The molecules thus identified can be employed to increase metabolic rate and enhance weight loss.

In the treatment of cachexia, those skilled in the art will appreciate that the modulation of mitochonrial membrane potential may be used to decrease body metabolic rate, thereby enhancing an individual's ability for weight gain. Screening assays may be conducted to identify molecules which can down-regulate expression or activity (such as the uncoupling) of human OGC. Molecules that down-regulate human OGC activity thereby increase mitochondrial membrane potential. The molecules thus identified can then be employed to decrease metabolic rate and enhance weight gain.

Human OGC may also be employed in diagnostic methods. For example, the presence or absence of human OGC activity, or alternatively over- or under-expression of human OGC in an individual's cells, can be detected. The skilled practitioner may use information resulting from such detection assays to assist in predicting metabolic conditions or risk for onset of obesity. If it is determined, for instance, that human OGC activity in a patient is abnormally high or low, therapy such as hormone therapy or gene therapy could be administered to return the human OGC activity or expression to a physiologically acceptable state.

Accordingly, the human OGC molecules described in the application may be useful in diagnostic methods. For example, the presence or absence of human OGC activity, or alternatively over- or under-expression, in an individual's cells or tissues, can be detected using assays known in the art, including those described in the Examples below. The invention provides a method of detecting expression of human OGC (or its isoforms) in a mammalian cell or tissue sample, comprising contacting a mammalian cell or tissue sample with a DNA probe and analyzing expression of human OGC mRNA transcript in said sample. Quantitative RT-PCR methods using DNA primers and probes which are isoform specific may also be employed to assist in quantitating specific isoform mRNA abundance. Further, DNA array technologies in the art may be employed to quantitate one or more isoform(s) RNA abundance. The sample may comprise various mammalian cells or tissues, including but not limited to, liver tissue, white adipose tissue and skeletal muscle. The skilled practitioner may use information resulting from such detection assays to assist in predicting metabolic conditions or onset of obesity. If it is determined, for instance, that human OGC expression (or abundance) levels or distribution levels in a patient are abnormally high or low as compared to a control population of mammals of corresponding age and normal body weight (or alternatively, to a population of mammals diagnosed as being obese), therapy such as gene therapy, diet control, etc. may be employed to treat the mammal.

Detection of impaired human OGC expression or function in the mammal may also be used to assist in diagnosing or treating impaired neural activity or neural degeneration. It is known in the art that reactive oxygen species can cause cellular damage in various tissues, particularly in brain tissue, and more particularly in brain neuronal tissue. An increase in the presence or generation of reactive oxygen species has been associated with Down's syndrome, as well as other neurodegenerative diseases. It is believed that human OGC or its isoforms can regulate the generation of reactive oxygen species and may play a protective role.

Accordingly, in the treatment of the conditions described above, those skilled in the art will appreciate that the modulation of human OGC expression or activity may be used to, for instance, increase body metabolic rate, thereby enhancing an individual's ability for weight loss. Screening assays may be conducted to identify molecules which can up-regulate expression or activity (such as the uncoupling) of human OGC. The molecules thus identified can then be employed to increase metabolic rate and enhance weight loss. The human OGC polypeptides are useful in assays for identifying lead compounds for therapeutically active agents that modulate expression or activity of human OGC. Candidate molecules or compounds may be assayed with the mammals' cells or tissues to determine the effect(s) of the candidate molecule or compound on human OGC expression or activity. Such screening assays may be amenable to high-throughput screening of chemical libraries, and are particularly suitable for identifying small molecule drug candidates. Small molecules include but are not limited to synthetic organic or inorganic compounds. The assays can be performed in a variety of formats, including protein-protein binding assays, biochemical screening assays, immunoassays, cell based assays, etc. Such assay formats are well known in the art.

Accordingly, in one embodiment, there is provided a method of conducting a screening assay to identify a molecule which enhances or up-regulates either activity and/or expression of human OGC, comprising the steps of exposing a mammalian cell or tissue sample believed to comprise human OGC to a candidate TO molecule and subsequently analyzing expression and/or activity of human OGC in said sample. In this method, the sample may be further analyzed for mitochondrial membrane potential. Optionally, the human OGC is a native polypeptide or any of the specific isoforms of human OGC identified herein. The sample being analyzed may comprise various mammalian cells or tissues, including but not limited to human brain tissue and adipose tissue. The screening assay may be an in vitro or in vivo assay. By way of example, an in vivo screening assay may be conducted in a transgenic animal wherein a promoter for a human OGC gene may be linked to a reporter gene such as luciferase or beta-galactosidase. Optionally, "knock in" technology may be used in this regard in which such a reporter gene is inserted 5' to the promoter (which in turn is linked to a genomic sequence encoding a human OGC). Such techniques are known in the art. The candidate molecule employed in the screening assay may be a small molecule comprising a synthetic organic or inorganic compound. In an alternative embodiment, the screening assay is conducted to identify a molecule which decreases or down-regulates activity and/or expression of human OGC. The effect(s) that such candidate molecule may have on the expression and/or activity of human OGC may be compared to a control or reference sample, such as for instance, expression or activity of human OGC observed in a like mammal.

B. Pharmaceutical Compositions

Agonists or antagonists of human OGC can be incorporated into pharmaceutical compositions. Such compositions typically comprise the agonists or antagonists and a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration (Gennaro, 2000). Preferred examples of such carriers or diluents include, but are not limited to, water, saline, Finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

1. General Considerations

A pharmaceutical composition of the agonist or antagonist is formulated to be compatible with its intended route of administration, including intravenous, intradermal, subcutaneous, oral (e.g., inhalation), transdermal (i.e., topical), transmucosal, and rectal administration. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

2. Injectable Formulations

Pharmaceutical compositions suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents, for example, parabens, chlorobutanol, phenol, ascorbic acid, and thimerosal, can contain microorganism contamination. Isotonic agents, for example, sugars, polyalcohols such as manitol, sorbitol, and sodium chloride can be included in the composition. Compositions that can delay absorption include agents such as aluminum monostearate and gelatin.

Sterile injectable solutions can be prepared by incorporating the active compound in the required amount in an appropriate solvent with one or a combination of ingredients as required, followed by sterilization. Generally, dispersions are prepared by incorporating the active compound into a sterile vehicle that contains a basic dispersion medium, and the other required ingredients. Sterile powders for the preparation of sterile injectable solutions, methods of preparation include vacuum drying and freeze-drying that yield a powder containing the active ingredient and any desired ingredient from a sterile solutions.

3. Oral Compositions

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring.

4. Compositions For Inhalation

For administration by inhalation, the compounds are delivered as an aerosol spray from a nebulizer or a pressurized container that contains a suitable propellant, e.g., a gas such as carbon dioxide.

5. Systemic Administration

Systemic administration can also be transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams.

The compounds can also be prepared in the form of suppositories (e.g., with bases such as cocoa butter and other glycerides) or retention enemas for rectal delivery.

6. Carriers

In one embodiment, the active compounds are prepared with carriers that protect the compound against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from ALZA Corporation (Mountain View, Calif.) and NOVA Pharmaceuticals, Inc. (Lake Elsinore, Calif.), or prepared by one of skill in the art. Liposomal suspensions can also be used as pharmaceutically acceptable carriers. These can be prepared according to methods known to those skilled in the art, such as in (Eppstein et al., U.S. Pat. No. 4,522,811, 1985).

7. Unit Dosage

Oral formulations or parenteral compositions in unit dosage form can be created to facilitate administration and dosage uniformity. Unit dosage form refers to physically discrete units suited as single dosages for the subject to be treated, containing a therapeutically effective quantity of active compound in association with the required pharmaceutical carrier. The specification for the unit dosage forms of the invention are dictated by, and directly dependent on, the unique characteristics of the active compound and the particular desired therapeutic effect, and the inherent limitations of compounding the active compound.

8. Gene Therapy Compositions

The nucleic acid molecules encoding human OGC can be inserted into vectors and used as gene therapy vectors. Gene therapy vectors can be delivered to a subject by, for example, intravenous injection, local administration (Nabel and Nabel, U.S. Pat. No. 5,328,470, 1994), or by stereotactic injection (Chen et al., 1994). The pharmaceutical preparation of a gene therapy vector can include an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

9. Dosage

The pharmaceutical composition may further comprise other therapeutically active compounds as noted herein which are usually applied in the treatment of human OGC-related conditions.

In the treatment or prevention of conditions which require human OGC modulation an appropriate dosage level of an agonist or antagonist will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

However, the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

10. Kits For Pharmaceutical Compositions

The pharmaceutical compositions can be included in a kit, container, pack, or dispenser together with instructions for administration to treat a metabolic disorder or disease. When the invention is supplied as a kit, the different components of the composition may be packaged in separate containers and admixed immediately before use. Such packaging of the components separately may permit long-term storage without losing the active components' functions.

Kits may also include reagents in separate containers that facilitate the execution of a specific test, such as diagnostic tests or tissue typing. For example, human OGC DNA templates and suitable primers may be supplied for internal controls.

(a) Containers or Vessels

The reagents included in kits can be supplied in containers of any sort such that the life of the different components are preserved, and are not adsorbed or altered by the materials of the container. For example, sealed glass ampules may contain lyophilized human OGC or buffer that have been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

(b) Instructional Materials

Kits may also be supplied with instructional materials. Instructions may be printed on paper or other substrate, and/or may be supplied as an electronic-readable medium, such as a floppy disc, CD-ROM, DVD-ROM, Zip disc, videotape, laserdisc, audio tape, etc. Detailed instructions may not be physically associated with the kit; instead, a user may be directed to an internet web site specified by the manufacturer or distributor of the kit, or supplied as electronic mail.

C. Full-length Human OGC

In certain embodiments of the present invention, an isolated nucleotide sequence encoding a polypeptide referred to in the present application as human OGC is utilized. In preferred embodiments, the nucleotide sequence is that of GenBank Accession Number NM_003562 (Table 1) and AF070548 (Table 2), with the nucleotide sequence of AF070548 being most preferred. For sake of simplicity, in the present specification the protein encoded by AF070548 as well as all further native homologues and variants included in the foregoing definition of human OGC, will be referred to as "human OGC," regardless of their origin or mode of preparation.

TABLE 1

NM_003562 (SEQ ID NO:1)

CCGAGGGCCATTGAGTGGCGATGGCGGCGACGGCGAGTGCCGGGGCCGGCGGGATGGACGGGAAGCCCCG

TACCTCCCCTAAGTCCGTCAAGTTCCTGTTTGGGGGCCTGGCCGGGATGGGAGCTACAGTTTTTGTCCAG

CCCCTGGACCTGGTGAAGAACCGGATGCAGTTGAGCGGGGAAGGGGCCAAGACTCGAGAGTACAAAACCA

GCTTCCATGCCCTCACCAGTATCCTGAAGGCAGAAGGCCTGAGGGGCATTTACACTGGGCTGTCGGCTGG

CCTGCTGCGTCAGGCCACCTACACCACTACCCGCCTTGGCATCTATACCGTGCTGTTTGAGCGCCTGACT

GGGGCTGATGGTACTCCCCCTGGCTTTCTGCTGAAGGCTGTGATTGGCATGACCGCAGGTGCCACTGGTG

CCTTTGTGGGAACACCAGCCGAAGTGGCTCTTATCCGCATGACTGCCGATGGCCGGCTTCCAGCTGACCA

GCGCCGTGGCTACAAAAATGTGTTTAACGCCCTGATTCGAATCACCCGGGAAGAGGGTGTCCTCACACTG

TGGCGGGGCTGCATCCCTACCATGGCTCGGGCCGTCGTCGTCAATGCTGCCCAGCTCGCCTCCTACTCCC

AATCCAAGCAGTTCTTACTGGACTCAGGCTACTTCTCTGACAACATCCTGTGCCACTTCTGTGCCAGCAT

GATCAGCGGTCTTGTCACCACTGCTGCCTCCATGCCTGTGGACATTGCCAAGACCCGAATCCAGAACATG

TABLE 1-continued

NM_003562 (SEQ ID NO:1)

CGGATGATTGATGGGAAGCCGGAATACAAGAACGGGCTGGACGTGCTGTTCAAAGTTGTCCGCTACGAGG

GCTTCTTCAGCCTGTGGAAGGGCTTCACGCCGTACTATGCCCGCCTGGGCCCCCACACCGTCCTCACCTT

CATCTTCTTGGAGCAGATGAACAAGGCCTACAAGCGTCTCTTCCTCAGTGGCTGAAGCGTTTCAGGGCAC

ACAGGACAGCAGAAGATCCCCTTTGTCAGTGGGGAAACCAAGGCAGAGCTGAGGGGACAGGGAGGAGCAG

AAGCCATCAAGATGGTCAAAGGGCCTGCAGAGGGAGATGTGGCCTTCCTCCCCCTCATTGAGGACTCAAT

AAA

TABLE 2

AF070548 (SEQ ID NO:2)

CCTCGTGCCAGGCGTGCGCGCGCCCTCGCTCTGTTGCGCGCGCGGTGTCACCTTGGGCGCGAGCGGGCC

GTGCGCGCACGGGACCCGGAGCCGAGGGCCATTGAGTGGCGATGGCGGCGACGGCGAGTGCCGGGCCGG

CGGGATAGACGGGAAGCCCCGTACCTCCCCTAAGTCCGTCAAGTTCCTGTTTGGGGGCCTGGCCGGGATG

GGAGCTACAGTTTTTGTCCAGCCCCTGGACCTGGTGAAGAACCGGATGCAGTTGAGCGGGGAAGGGCCA

AGACTCGAGAGTACAAAACCAGCTTCCATGCCCTCACCAGTATCCTGAAGGCAGAAGGCCTGAGGGCAT

TTACACTGGGCTGTCGGCTGGCCTGCTGCGTCAGGCCACCTACACCACTACCCGCCTTGGCATCTATACC

GTGCTGTTTGAGCGCCTGACTGGGGCTGATGGTACTCCCCCTGGCTTTCTGCTGAAGGCTGTGATTGGCA

TGACCGCAGGTGCCACTGGTGCCTTTGTGGGAACACCAGCCGAAGTGGCTCTTATCCGCATGACTGCCGA

TGGCCGGCTTCCAGCTGACCAGCGCCGTGGCTACAAAAATGTGTTTAACGCCCTGATTCGAATCACCCGG

GAAGAGGGTGTCCTCACACTGTGGCGGGGCTGCATCCCTACCATGGCTCGGGCCGTCGTCGTCAATGCTG

CCCAGCTCGCCTCCTACTCCCAATCCAAGCAGTTCTTACTGGACTCAGGCTACTTCTCTGACAACATCTT

GTGCCACTTCTGTGCCAGCATGATCAGCGGTCTTGTCACCACTGCTGCCTCCATGCCTGTGGACATTGCC

AAGACCCGAATCCAGAACATGCGGATGATTGATGGGAAGCCGGAATACAAGAACGGGCTGGACGTGCTGT

TCAAAGTTGTCCGCTACGAGGGCTTCTTCAGCCTGTGGAAGGGCTTCACGCCGTACTATGCCCGCCTGGG

CCCCCACACCGTCCTCACCTTCATCTTCTTGGAGCAGATGAACAAGGCCTACAAGCGTCTCTTCCTCAGT

GGCTGAAGCGGCCGGGGGCTCCCACTCGCCTGCTGCGCCTATAGCCACTGCGCCCTGGGGCCTGGGCTC

TGCTGCCCTGGACCCCTCTATTTATTTCCCTTCCACAGTGTGGTTTCTTCCTCTGCGGTAAAGGACTTGG

TCTGTTCTACCCCCTGCTCCAGCTTGCCCTGCTCGTCCTGATCCTGTGATTTCTCTGTCCTTGGCTATTC

TTGCAGGGAGCTGGAAAACTTCCTGAGGATTTCTGGCCTCCCCCTGGGTTTTAGTTTCAGGGCACACAGG

ACAGCAGAAGATCCCCTTTGTCAGTGGGGAAACCAAGGCAGAGCTGAGGGGACAGGGAGGAGCAGAAGCC

ATCAAGATGGTCAAAGGGCCTGCAGAGGGAGATGTGGCCCTTCCTCCCCCTCATTGAGGACTTAATAAAT

TGGATTGATGACACCAAAAAAAAAAAAAAAAAA

D. Human OGC Variants

In addition to the full-length native sequence of human OGC polypeptides described herein, it is contemplated that human OGC variants can be useful. Human OGC variants can be prepared by introducing appropriate nucleotide changes into the human OGC DNA, and/or by synthesis of the desired human OGC polypeptide. Those skilled in the art will appreciate that amino acid changes may alter post-translational processes of the human OGC, such as changing the number or position of glycosylation sites or altering the membrane anchoring characteristics.

Variations in the native full-length sequence human OGC or in various domains of the human OGC described herein, can be made, for example, using any of the techniques and guidelines for conservative and non-conservative mutations set forth, for instance, in U.S. Pat. No. 5,364,934. Variations may be a substitution, deletion or insertion of one or more codons encoding the human OGC that results in a change in the amino acid sequence of the human OGC as compared with the native sequence human OGC. Optionally the variation is by substitution of at least one amino acid with any other amino acid in one or more of the domains of the human OGC. Guidance in determining which amino acid residue may be inserted, substituted or deleted without adversely affecting the desired activity may be found by comparing the sequence of the human OGC with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and, if desired, testing the resulting variants for activity in assays known in the art or as described herein.

One embodiment of the invention is directed to human OGC variants which are fragments of the full length human OGC. Preferably, such fragments retain a desired activity or property of the full length human OGC.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the human OGC variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081–1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

E. Modifications of Human OGC

Use of covalent modifications of human OGC are included within the scope of this invention. One type of covalent modification includes reacting targeted amino acid residues of a human OGC polypeptide with an organic derivatizing agent that is capable of reacting with selected side chains or the N- or C-terminal residues of the human OGC. Derivatization with bifunctional agents is useful, for instance, for crosslinking human OGC to a water-insoluble support matrix or surface for use in the method for purifying anti-human OGC antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of the human OGC polypeptide included within the scope of this invention comprises altering the native glycosylation pattern of the polypeptide. "Altering the native glycosylation pattern" is intended for purposes herein to mean deleting one or more carbohydrate moieties found in native sequence human OGC (either by removing the underlying glycosylation site or by deleting the glycosylation by chemical and/or enzymatic means), and/or adding one or more glycosylation sites that are not present in the native sequence human OGC. In addition, the phrase includes qualitative changes in the glycosylation of the native proteins, involving a change in the nature and proportions of the various carbohydrate moieties present.

Addition of glycosylation sites to the human OGC polypeptide may be accomplished by altering the amino acid sequence. The alteration may be made, for example, by the addition of, or substitution by, one or more serine or threonine residues to the native sequence human OGC (for O-linked glycosylation sites). The human OGC amino acid sequence may optionally be altered through changes at the DNA level, particularly by mutating the DNA encoding the human OGC polypeptide at preselected bases such that codons are generated that will translate into the desired amino acids.

Another means of increasing the number of carbohydrate moieties on the human OGC polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the human OGC polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of human OGC comprises linking the human OGC polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The human OGC may also be modified in a way to form a chimeric molecule comprising human OGC fused to another, heterologous polypeptide or amino acid sequence.

In one embodiment, such a chimeric molecule comprises a fusion of the human OGC with a tag polypeptide which provides an epitope to which an anti-tag antibody can selectively bind. The epitope tag is generally placed at the amino- or carboxyl-terminus of the human OGC. The presence of such epitope-tagged forms of the human OGC can be detected using an antibody against the tag polypeptide. Also, provision of the epitope tag enables the human OGC to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

In an alternative embodiment, the chimeric molecule may comprise a fusion of the human OGC with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a human OGC polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

The human OGC may also be modified in a way to form a chimeric molecule comprising human OGC fused to a leucine zipper. Various leucine zipper polypeptides have been described in the art. See, e.g., Landschulz et al., *Science*, 240:1759 (1988); WO 94/10308; Hoppe et al., *FEBS Letters*, 344:1991 (1994); Maniatis et al., *Nature*, 341:24 (1989). Those skilled in the art will appreciate that the leucine zipper may be fused at either the 5' or 3' end of the human OGC molecule.

F. Preparation of Human OGC

The description below relates primarily to production of human OGC by culturing cells transformed or transfected with a vector containing human OGC nucleic acid. It is, of course, contemplated that alternative methods, which are well known in the art, may be employed to prepare human OGC. For instance, the human OGC sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the human OGC may be chemically synthesized separately and combined using chemical or enzymatic methods to produce the full-length human OGC.

1. Isolation of DNA Encoding Human OGC

Vectors containing human OGC are commercially available (InCyte Pharmaceuticals; Palo Alto, Calif.). Alternatively, DNA encoding human OGC may be obtained from a cDNA library prepared from tissue believed to possess the human OGC mRNA and to express it at a detectable level. Accordingly, human human OGC DNA can be conveniently obtained from a cDNA library prepared from human tissue. The human OGC-encoding gene may also be obtained from a genomic library or by oligonucleotide synthesis.

Libraries can be screened with probes (such as antibodies to the human OGC or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding human OGC is to use PCR methodology [Sambrook et al., supra; Dieffenbach et al., *PCR Primer: A Laboratory Manual* (Cold Spring Harbor Laboratory Press, 1995)].

Methods of screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra, and are described above in Section I.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as BLAST, BLAST2, ALIGN, DNAstar, and INHERIT to measure identity or positives for the sequence comparison.

2. Selection and Transformation of Host Cells

Host cells are transfected or transformed with expression or cloning vectors described herein for human OGC production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, CaPO$_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium*

*tumefaciens* is used for transformation of certain plant cells, as described by Shaw et al., *Gene,* 23:315 (1983) and WO 89/05859 published Jun. 29, 1989. For mammalian cells without such cell walls, the calcium phosphate precipitation method of Graham and van der Eb, *Virology,* 52:456–457 (1978) can be employed. General aspects of mammalian cell host system transformations have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci. (USA),* 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology,* 185:527–537 (1990) and Mansour et al., *Nature,* 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635).

In addition to prokaryotes, eukaryotic microbes such as filamentous fungi or yeast are suitable cloning or expression hosts for human OGC-encoding vectors. *Saccharomyces cerevisiae* is a commonly used lower eukaryotic host microorganism.

Suitable host cells for the expression of glycosylated human OGC are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); Chinese hamster ovary cells/-DHFR (CHO, Urlaub and Chasin, *Proc. Natl. Acad. Sci. USA,* 77:4216 (1980)); mouse sertoli cells (TM4, Mather, Biol. Reprod., 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding human OGC may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The human OGC may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the human OGC-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2 μm plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the human OGC-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the human OGC-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21–25 (1983)].

Promoters for use in bacterial systems also will contain a Shine-Dalgarno (S.D.) sequence operably linked to the DNA encoding human OGC.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Human OGC transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the human OGC by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the human OGC coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding human OGC.

Still other methods, vectors, and host cells suitable for adaptation to the synthesis of human OGC in recombinant vertebrate cell culture are described in Gething et al., *Nature*, 293:620–625 (1981); Mantei et al., *Nature*, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence human OGC polypeptide or against a synthetic peptide or against exogenous sequence fused to human OGC DNA and encoding a specific antibody epitope.

5. Purification of Polypeptide

Forms of human OGC may be recovered from culture medium or from host cell lysates. If membrane-bound, it can be released from the membrane using a suitable detergent solution (e.g. Triton-X 100) or by enzymatic cleavage. Cells employed in expression of human OGC can be disrupted by various physical or chemical means, such as freeze-thaw cycling, sonication, mechanical disruption, or cell lysing agents.

It may be desired to purify human OGC from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the human OGC. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular human OGC produced.

G. Anti-human OGC Antibodies

In certain embodiments, anti-human OGC antibodies may be utilized. Exemplary antibodies include polyclonal, monoclonal, humanized, bispecific, and heteroconjugate antibodies.

1. Polyclonal Antibodies

The anti-human OGC antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the human OGC polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-human OGC antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the human OGC polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against human OGC. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-human OGC antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522–525 (1986); Riechmann et al., Nature, 332:323–329 (1988); and Presta, Curr. Op. Struct. Biol., 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522–525 (1986); Riechmann et al., Nature, 332:323–327 (1988); Verhoeyen et al., Science, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol. 222:581 (1991)]. The techniques of Cole et al. and Boemer et al. are also available for the preparation of human monoclonal antibodies (Cole et al., Monoclonal Antibodies and Cancer Therapy, Alan R. Liss, p. 77 (1985) and Boerner et al., J. Immunol., 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., Bio/Technology 10, 779–783 (1992); Lonberg et al., Nature 368 856–859 (1994); Morrison, Nature 368 812–13 (1994); Fishwild et al., Nature Biotechnology 14, 845–51 (1996); Neuberger, Nature Biotechnology 14, 826 (1996); Lonberg and Huszar, Intern. Rev. Immunol. 1365–93 (1995).

4. Bispecific Antibodies

Bispecific antibodies are monoclonal, preferably human or humanized, antibodies that have binding specificities for at least two different antigens. In the present case, one of the binding specificities is for the human OGC, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

H. Uses For Anti-human OGC Antibodies

The anti-human OGC antibodies of the invention have various utilities. For example, anti-human OGC antibodies may be used in diagnostic assays for human OGC, e.g., detecting its expression in specific cells or tissues. Various diagnostic assay techniques known in the art may be used, such as competitive binding assays, direct or indirect sandwich assays and immunoprecipitation assays conducted in either heterogeneous or homogeneous phases [Zola, Monoclonal Antibodies: A Manual of Techniques, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or 125I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-human OGC antibodies also are useful for the affinity purification of human OGC from recombinant cell culture or natural sources. In this process, the antibodies against human OGC are immobilized on a suitable support, such as Sephadex resin or filter paper, using methods well known in the art. The immobilized antibody then is contacted with a sample containing the human OGC to be purified, and thereafter the support is washed with a suitable solvent that will remove substantially all the material in the sample except the human OGC, which is bound to the immobilized antibody. Finally, the support is washed with another suitable solvent that will release the human OGC from the antibody.

The following examples are offered for illustrative purposes only, and are not intended to limit the scope of the present invention in any way.

All patent and literature references cited in the present specification are hereby incorporated by reference in their entirety.

EXAMPLE 1

This Example describes the surprising ability of human OGC to act as an uncoupling protein. Overexpression of human OGC in 293 cells decreased $\Delta_{\Psi_m}$ in the cells as powerfully as UCP3. Thus, human OGC may affect metabolism by altering respiration in cells.

In a set of experiments to determine whether a putative UCP, when overexpressed, could lower $\Delta_{\Psi_m}$, human OGC was chosen as a negative control. This approach was logical based on the electroneutral nature of 2-oxoglutarate$^{2-}$/malate$^{2-}$ exchange catalyzed by the carrier [see Indiveri et al., (1987) J. Biol. Chem. 262(33):15979–15983.], its clear localization to the mitochondrial inner membrane [Palmisano et al., (1998) Biochem. J. 333:151–158], and its reported lack of effect on mitochondrial function in OGC-transformed yeast [Sanchis et al., (1998). J. Biol. Chem. 273(51): 34611–34615].

Surprisingly, overexpression of the human OGC significantly diminished $\Delta_{\Psi_m}$, signaling a previously-unappreciated uncoupling activity of this protein. Indeed, OGC was almost as powerful as UCP3 in eliciting a drop in $\Delta_{\Psi_m}$ of 293 cells, as judged by the number of cells displaying lowered $\Delta_{\Psi_m}$. Based on such results, one may not exclude the possibility that OGC (and perhaps other carriers not currently thought to have uncoupling activity) could influence global proton leak in mammals.

Materials and Methods used in this Example

Expression Constructs

A full-length human 2-oxoglutarate cDNA cloned in pINCY (Clone 2581467; pINCY-huOGC) was purchased from InCyte Pharmaceuticals (Palo Alto, Calif., USA), and subcloned into pRK5E for expression analyses (pRK5E-huOGC). Compared to the published sequence [Iacobazzi, V., Palmieri, F., Runswick, M. J., and Walker, J. E. (1992). DNA Sequence 3:79–88](GenBank accession NM_003562), pRK5E-huOGC displays a difference (G→A) at position 36 (relative to start ATG) encoding a protein with a single amino acid difference (M12I). However, pRK5E-huOGC matches clone 24408 in the public database (GenBank accession AF070548). Furthermore, pRK5E-huOGC encodes the most abundant form of OGC in man, as perusal of the InCyte and public EST databases indicate that the pRK5E-huOGC protein sequence matches corresponding regions of ESTs derived from at least 22 separate human cDNA libraries (whereas the published sequence did not match any EST at amino acid position 12). Construction of the pcDNA3-UCP3 expression vector is described elsewhere [Mao, W., Yu, X. X., Zhong, A., Li, W., Brush, J., Sherwood, S. W., Adams, S. H., and Pan, G. (1999) FEBS Letters 443: 326–330.].

Mitochondrial Membrane Potential Measurements

Transfections and measurements of $\Delta_{\Psi_m}$ were carried out using protocols described previously [Yu et al., FASEB J 2000 August; 14(11):1611–8]. 293 cells were co-transfected with pGreen Lantern-1 (green fluorescent protein, GFP; GIBCO BRL) along with pRK7 vector alone (control) or expression vectors containing human OGC or UCP3 (see above). Approximately 24 hr later, treatment-related differences in $\Delta_{\Psi_m}$ were determined in green-fluorescent protein (GFP) positive cells by monitoring changes in the fluorescence intensity of the $\Delta_{\Psi_m}$-sensitive dye TMRE (tetramethylrhodamine ethyl ester; Molecular Probes, Eugene, Oreg., USA). The degree of diminution of the $\Delta_{\Psi_m}$ was assessed by the shift in the relative number of cells displaying lowered $\Delta_{\Psi_m}$. The transfection protocols employed herein resulted in at least a 30-fold overexpression of each gene as judged by real-time RT-PCR analysis of mRNA abundance.

The invention claimed is:

1. A method for screening for compounds that affect mitochondrial uncoupling, comprising:
   a) contacting a mammalian cell or tissue sample in vitro with a candidate compound;
   b) analyzing the contacted mammalian cell or tissue sample for expression of a polypeptide having at least 95% amino acid sequence identity to the polypeptide encoded by SEQ ID NO:2, wherein the polypeptide having at least 95% sequence identity has mitochondrial uncoupling activity; and
   c) analyzing mitochondrial membrane potential of the contacted mammalian cell or tissue sample,
   wherein a change in mitochondrial membrane potential and a change in expression of the polypeptide having at least 95% sequence identity, as compared to a control cell not treated with the candidate compound indicates that the compound affects mitochondrial uncoupling.

2. The method of claim 1, wherein the mammalian cell or tissue sample is a human cell or tissue sample.

3. The method of claim 2, wherein the analyzing of expression of the polypeptide comprises analyzing expression of the polypeptide encoded by SEQ ID NO:2.

4. The method of claim 1, wherein the candidate compound is a member selected from the group consisting of a small molecule, a polynucleotide, a modified polynucleotide, a polypeptide, an antibody, an antibody fragment and a modified antibody.

5. A method for screening for compounds that affect mitochondrial uncoupling, comprising:
   a) contacting a mammalian cell or tissue sample in vitro with a candidate compound; and
   b) analyzing the contacted mammalian cell or tissue sample for expression of a polypeptide having at least 95% sequence identity to a the polypeptide encoded by SEQ ID NO:2,
   wherein a change in expression of the polypeptide as compared to a control cell not contacted with the candidate compound indicates that the compound affects mitochondrial uncoupling.

6. The method of claim 5, wherein the mammalian cell or tissue sample is a human cell or tissue sample.

7. The method of claim 5, wherein the analyzing of expression of the polypeptide comprises analyzing expression of the polypeptide encoded by SEQ ID NO:2.

8. The method of claim 5, wherein the candidate compound is a member selected from the group consisting of a small molecule, a polynucleotide, a modified polynucleotide, a polypeptide, an antibody, an antibody fragment and a modified antibody.

9. The method of claim 1, wherein the mammalian cell or tissue sample is a liver cell or tissue sample, white adipose cell or tissue sample, or skeletal muscle cell or tissue sample.

10. The method of claim 5, wherein the mammalian cell or tissue sample is a liver cell or tissue sample, white adipose cell or tissue sample, or skeletal muscle cell or tissue sample.

* * * * *

UNITED STATES PATENT AND TRADEMARK OFFICE
CERTIFICATE OF CORRECTION

| | | |
|---|---|---|
| PATENT NO. | : 7,141,421 B2 | Page 1 of 1 |
| APPLICATION NO. | : 09/888264 | |
| DATED | : November 28, 2006 | |
| INVENTOR(S) | : Adams et al. | |

It is certified that error appears in the above-identified patent and that said Letters Patent is hereby corrected as shown below:

Col. 31, line 4: "125I" should read --$^{125}$I--

Claim 5, Col. 36, line 23: "to a the polypeptide" should read --to the polypeptide--

Signed and Sealed this

Thirteenth Day of February, 2007

JON W. DUDAS
*Director of the United States Patent and Trademark Office*